United States Patent
Matsunaga et al.

(10) Patent No.: US 7,196,213 B2
(45) Date of Patent: Mar. 27, 2007

(54) PROCESS FOR PRODUCING PHOSPHATE

(75) Inventors: Akira Matsunaga, Wakayama (JP); Satoru Kijima, Wakayama (JP)

(73) Assignee: Kao Corporation, Tokyo (JP)

( * ) Notice: Subject to any disclaimer, the term of this patent is extended or adjusted under 35 U.S.C. 154(b) by 490 days.

(21) Appl. No.: 10/742,817

(22) Filed: Dec. 23, 2003

(65) Prior Publication Data

US 2004/0186309 A1 Sep. 23, 2004

(30) Foreign Application Priority Data

Dec. 26, 2002 (JP) .............................. 2002-377463

(51) Int. Cl.
*C07C 9/02* (2006.01)
(52) U.S. Cl. ...................... 558/104; 558/110
(58) Field of Classification Search .................. 558/70, 558/104, 110
See application file for complete search history.

(56) References Cited

U.S. PATENT DOCUMENTS

| | | | |
|---|---|---|---|
| 4,845,239 A | 7/1989 | Wakatsuki et al. | |
| 4,866,193 A | 9/1989 | Uphues et al. | |
| 4,985,412 A | 1/1991 | Matsunaga et al. | |
| 5,071,585 A | 12/1991 | Matsunaga et al. | |
| 5,883,280 A | 3/1999 | Tsuyutani et al. | |
| 6,034,261 A | 3/2000 | Matsunaga et al. | |
| 6,407,277 B1 * | 6/2002 | Matsunaga et al. | 558/110 |

FOREIGN PATENT DOCUMENTS

| | | |
|---|---|---|
| DE | 36 43 761 | 6/1988 |
| JP | 62-25155 | 6/1987 |
| JP | 63-166893 | 7/1988 |
| JP | 3-27558 | 4/1991 |
| JP | 7-48244 | 2/1995 |
| JP | 11-158193 | 6/1999 |

* cited by examiner

*Primary Examiner*—James O. Wilson
*Assistant Examiner*—Ebenezer Sackey
(74) *Attorney, Agent, or Firm*—Oblon, Spivak, McClelland, Maier & Neustadt, P.C.

(57) ABSTRACT

Provided are a process for producing a phosphate and a process for stabilizing a phosphate, the phosphate being an acid-form phosphate wherein an organic hydroxy compound is an alkylene oxide adduct. A production process of a phosphate and a stabilization process of a phosphate, including the step 1 of reacting an organic hydroxy compound represented by the following general formula (I) with a phosphorylating agent:

$$R^1 \text{—} O \text{—} (AO)_n \text{—} H \quad (I)$$

wherein $R^1$ represents a straight or branched alkyl group or alkenyl group having 6 to 36 carbon atoms, AO represents an oxyalkylene group having 2 to 4 carbon atoms, and n is a number of 0.1 to 100 on the average; the step 2 of purifying the reaction product obtained in the step 1 until the content of the organic hydroxy compound that has not yet reacted becomes 2% or less by weight; and the step 3 of adding water to the purified product obtained in the step 2 at such a ratio that the content of water in the final product is from 0.5 to 10% by weight.

19 Claims, No Drawings

PROCESS FOR PRODUCING PHOSPHATE

FIELD OF THE INVENTION

The present invention relates to a process for producing a phosphate and a process for stabilizing a phosphate.

PRIOR ARTS

A phosphate of an organic hydroxy compound is used in the fields of detergents, emulsifiers, fiber treating agents, rust inhibitors or medical supplies. In particular, a phosphate using an alkylene oxide adduct as the organic hydroxy compound is excellent in foaming force or detergency within the range of weak acidity and further has low toxicity or skin irritation. Therefore, the phosphate is useful for goods used directly for the human body, such as shampoo or face washing agents, and is particularly useful for skin care products.

Usually, the phosphate can be obtained by reacting an organic hydroxy compound with a phosphorylating agent. However, it is unavoidable that the organic hydroxy compound remains. This remaining organic hydroxy compound produces a bad effect on the odor, the color tone, the irritation, and others of the resultant product. Hitherto, therefore, it has been necessary to perform purification for removing this compound after the phosphorylation of the organic hydroxy compound.

However, there is caused a problem that even if such purification is performed, the product generates an odor or the product is colored when the product is stored for a long period. In order to solve such problems, JP-A 7-48244 describes a method of adding, to an aqueous phosphate salt solution, a compound having chelating ability, such as an aminocarboxylic acid or a phosphonic acid. About the phosphate described in JP-A 7-48244, the organic hydroxy compound thereof is not any alkylene oxide adduct. Additionally, the phosphate is a phosphate salt in a salt form.

SUMMARY OF THE INVENTION

The present invention relates to a process for producing a phosphate, including the following steps 1, 2 and 3:

step 1: the step of reacting an organic hydroxy compound represented by the following general formula (I) with a phosphorylating agent:

$$R^1-O-(AO)_n-H \qquad (I)$$

wherein $R^1$ represents a straight or branched alkyl group or alkenyl group having 6 to 36 carbon atoms, AO represents an oxyalkylene group having 2 to 4 carbon atoms, and n is a number of 0.1 to 100 on the average;

step 2: the step of purifying the reaction product obtained in the step 1 until the content of the organic hydroxy compound that has not yet reacted becomes 2% or less by weight; and step 3: the step of adding water to the purified product obtained in the step 2 at such a ratio that the content of water in the final product is from 0.5 to 30% by weight.

The present invention also provides a process for stabilizing a phosphate, which includes adding water to a phosphate product obtained by reacting an organic hydroxy compound represented by the above-mentioned general formula (I) with a phosphorylating agent and subsequently purifying the resultant product until the content of the organic hydroxy compound that has not yet reacted becomes 2% or less by weight, at such a ratio that the content of water in the final product is from 0.5 to 30% by weight.

DETAILED EXPLANATION OF THE INVENTION

The acid-form phosphate wherein an organic hydroxy compound is an alkylene oxide adduct is excellent in foaming force or detergency within the range of weak acidity, and further can be made into a high concentration so that costs for transportation and others can be reduced. Blending variation thereof is also wide. It is therefore desired to supply such a phosphate stably.

The present invention relates to a process for producing an acid-form phosphate wherein an organic hydroxy compound is an alkylene oxide adduct and a process for stabilizing the phosphate, which make it possible to suppress generation of dioxane and prevent deterioration in smell at the time of storing the phosphate at high temperature.

The present invention relates to a process for producing an acid-form phosphate wherein an organic hydroxy compound is an alkylene oxide adduct thereto.

In the organic hydroxy compound represented by the general formula (I), used in the present invention, $R^1$ represents a straight or branched alkyl group or alkenyl group having 6 to 36 carbon atoms, and $R^1$ preferably has 8 to 30 carbon atoms and more preferably has 8 to 22 carbon atoms. AO represents an oxyalkylene group having 2 to 4 carbon atoms, and is preferably an oxyalkylene group having 2 to 3 carbon atoms, more preferably an oxyethylene group, or a mixed oxyalkylene group of an oxyethylene group and an oxypropylene group. n is a number of 0.1 to 100, which represents the average number of molecules of the alkylene oxide added, and n is preferably from 0.1 to 50, more preferably from 0.1 to 20.

Examples of the phosphorylating agent used in the present invention include orthophosphoric acid, phosphorus pentaoxide (phosphoric anhydride), polyphosphoric acid, phosphorus oxychloride and others. Orthophosphoric acid and phosphorus pentaoxide (phosphoric anhydride) are preferable. These may be used alone or in combination of two or more thereof.

In the step 1 of the present invention, the amount of the phosphorylating agent at the time of reacting the organic hydroxy compound with the phosphorylating agent can be appropriately decided in accordance with a target phosphate composition. The temperature at the time of reacting the organic hydroxy compound with the phosphorylating agent is preferably from 40 to 120° C., more preferably from 60 to 100° C. After the phosphorus oxidization reaction, it is preferable to conduct hydrolysis to decrease side products or such other.

In the step 2 of the present invention, purification is performed for removing the organic hydroxy compound that has not yet reacted, which generates a bad odor or the like, after the phosphorus oxidization reaction in the step 1. The content of this unreacted organic hydroxy compound is set to 2% or less by weight, preferably 1.5% or less by weight.

The method for the purification in the step 2 is not particularly limited. An example thereof is a method based on extraction or crystallization described in Japanese Patent Application Publication (JP-B) No. 3-27558 or JP-A No. 11-158193, or a method based on distillation, such as steam distillation, described in JP-B No. 62-25155 or JP-A No. 63-166893 or the like. Among these examples, distillation under reduced pressure is preferable, and further steam distillation, in particular, steam distillation using a forcible thin film type distillatory apparatus or the like is preferable.

In the step 3 of the present invention, water is added to the purified product obtained in the step 2, in which the content of the unreacted organic hydroxy compound is 2% or less by weight. The amount of water added at this time is varied by the amount of water present in the purified product obtained in the step 2. The content of water in the final product in the step 3 is 0.5% or more by weight, preferably 1.0% or more by weight from the viewpoint of suppressing the generation of dioxane, and is 30% or less by weight, preferably 10% or less by weight from the viewpoint of reducing transport costs and others.

In the step 3, it is preferable from the viewpoint of decreasing the viscosity and improving the stability at low temperature to add one or more selected from alcohols having 1 to 4 carbon atoms or glycols represented by the following general formula (II):

$$HO-(R^2O)_m-H \quad\quad (II)$$

wherein $R^2$ represents an alkylene group having 2 to 4 carbon atoms, and m is a number of 1 to 3.

Examples of the alcohols having 1 to 4 carbon atoms include methanol, ethanol, propanol, isopropanol and others, and examples of the glycols represented by the general formula (II) include ethylene glycol, propylene glycol, dipropylene glycol and others. The added amount of the one or more selected from the alcohols having 1 to 4 carbon atoms or the glycols represented by the general formula (II) is preferably from 0.1 to 30%, more preferably from 0.1 to 20% and particularly preferably from 0.5 to 10% by weight of the purified product obtained in the step 2.

In the step 3 of the present invention, it is preferable that an antioxidant is further added in order to prevent a deterioration in smell. Examples of the antioxidant include phenol type antioxidants, amine type antioxidants, sulfur type antioxidants, phosphorus type antioxidants and others. Phenol type antioxidants are preferable. Specific examples thereof include di-t-butylhydroxytoluene (BHT), di-t-butylhydroxyanisole (BHA), dl-α-tocopherol, isopropyl gallate and others. The added amount of these antioxidants is preferably from 0.0001 to 10%, more preferably from 0.0005 to 2% by weight of the purified product obtained in the step 2.

According to the production process of the present invention, it is possible to obtain a phosphate which prevents dioxane from being generated when the phosphate is stored at high temperature.

In storing, at a high temperature, an acid form phosphate in which an organic hydroxy compound constituting the phosphate is an alkylene oxide adduct, according to the stabilization process of the present invention, it is possible to suppress generation of dioxane.

The phosphate obtained by the process of the present invention is excellent in foaming force and detergency with the range of weak acidity and further exhibits a low toxicity and skin irritation. The smell thereof does not deteriorate. Therefore, the phosphate is very useful for various detergent bases, in particular, detergent bases for hands, faces and bodies. Since the resultant phosphate has a high concentration, transport costs can be reduced. Furthermore, various variations can be given at the time of incorporating the phosphate into detergents or the like since the phosphate is in an acid form.

According to the production process of the present invention, it is possible to obtain a phosphate which prevents dioxane from generating and has been improved in storage stability. According to the stabilization process of the present invention, it is possible to suppress generation of dioxane from a phosphate which includes an alkylene oxide adduct in an organic hydroxy compound which constitutes the phosphate and which is an acid form when the phosphate is stored at a high temperature. It is further prevented from deterioration in smell.

EXAMPLES

In the examples, % represents % by weight unless otherwise specified. The content of an unreacted organic hydroxy compound in a phosphate obtained in each Production Example and the water content therein were measured by the following methods.

Water Content in Phosphate:

A Karl Fischer electricity quantity titrator ("AQUA-COUNTER AQ-7", manufactured by Hiranuma Sangyo Co., Ltd.) was used to measure the water content.

Analysis of Unreacted Alcohol(ROH):

Triethanolamine was added to a phosphate to neutralize the phosphate, and subsequently an internal standard (for example, tetradecyl alcohol), a demulsifier (for example, ethanol), and petroleum ether were added thereto so as to extract the phosphate. An unreacted organic hydroxy compound in the petroleum ether was measured with a gas chromatograph ("HP-5890", manufactured by Agilent Co.).

Production Example 1

Into a 2000-mL reaction vessel were put 921.6 g (4.00 moles) of an organic hydroxy compound (average molecular weight=230.4) obtained by adding 1 mole of ethylene oxide to Kalcol 2098 (lauryl alcohol) made by Kao Corp., and 93.7 g of 85% by weight orthophosphoric acid (when the acid was represented by $P_2O_5 \cdot nH_2O$, $P_2O_5$: 0.41 mole, $H_2O$: 2.00 moles ), and then the resultant was stirred and mixed. While the temperature was kept at 50 to 70° C., 229.6 g (1.59 mole) of phosphorus pentaoxide (effective component: 98.5%) was gradually added thereto. Subsequently, the temperature was raised to 80° C. and reaction was conducted for 12 hours. Thereafter, the reaction product was subjected to deodorizing treatment using a steam distillatory apparatus (made of glass, heat conducting area: 0.03 m³) through a forcible thin film. The steam distillation was performed by supplying the reaction product and steam continuously at speeds of 100 g/hr. and 75 g/hr., respectively, at a jacket temperature of 150° C. at 2.67 kPa. As residues, a phosphate containing 0.8% of the organic hydroxy compound and 0.3% of water content was obtained.

Production Example 2

Into a 2000-mL reaction vessel were put 1330.8 g (1.50 moles) of an organic hydroxy compound (average molecular weight=887.2) obtained by adding 10 moles of propylene oxide to Kalcol 0898 (octyl alcohol) made by Kao Corp. and further adding 4 moles of ethylene oxide thereto, and 35.1 g of 85% by weight orthophosphoric acid (when the acid was represented by $P_2O_5 \cdot nH_2O$, $P_2O_5$: 0.15 mole, $H_2O$: 0.75 mole), and then the resultant was stirred and mixed. While the temperature was kept at 50 to 70° C., 86.5 g (0.60 mole) of phosphorus pentaoxide (effective component: 98.5%) was gradually added thereto. Subsequently, the temperature was raised to 80° C. and reaction was conducted for 12 hours.

Thereafter, the reaction product was subjected to deodorizing treatment using a steam distillatory apparatus (made of glass, heat conducting area: 0.03 m³) through a forcible thin film. The steam distillation was performed by supplying the reaction product and steam continuously at speeds of 100 g/hr. and 75 g/hr., respectively, at a jacket temperature of 150° C. at 2.67 kPa. As a residue, a phosphate containing 0.3% of the organic hydroxy compound and 0.3% of water content was obtained.

Production Example 3

Into a 2000-mL reaction vessel were put 1024.5 g (1.50 mole) of an organic hydroxy compound (average molecular weight=683.0) obtained by adding 10 moles of ethylene oxide to Kalcol 6098 (hexadecyl alcohol) made by Kao Corp., and 35.1 g of 85% by weight orthophosphoric acid (when the acid was represented by $P_2O_5 \cdot nH_2O$, $P_2O_5$: 0.15 mole, $H_2O$: 0.75 mole), and then the resultant was stirred and mixed. While the temperature was kept at 50 to 70° C., 86.5 g (0.60 mole) of phosphorus pentaoxide (effective component: 98.5%) was gradually added thereto. Subsequently, the temperature was raised to 80° C. and reaction was conducted for 12 hours. Thereafter, the reaction product was subjected to deodorizing treatment using a steam distillatory apparatus (made of glass, heat conducting area: 0.03 m³) through a forcible thin film. The steam distillation was performed by supplying the reaction product and steam continuously at speeds of 100 g/hr. and 75 g/hr., respectively, at a jacket temperature of 150° C. at 2.67 kPa. As a residue, a phosphate containing 1.2% of the organic hydroxy compound and 0.2% of water content was obtained.

Production Example 4

Into a 2000-mL reaction vessel were put 1125.6 g (4.00 moles) of an organichydroxycompound (average molecular weight=281.4) obtained by adding 2 moles of ethylene oxide to Dobanol 23 (average number of carbon atoms: 12.5, branching fraction: 25%) manufactured by Mitsubishi Chemical Corp., and 93.7 g of 85% by weight orthophosphoric acid (when the acid was represented by $P_2O_5 \cdot nH_2O$, $P_2O_5$: 0.41 mole, $H_2O$: 2.00 moles), and then the resultant was stirred and mixed. While the temperature was kept at 50 to 70° C., 229.6 g (1.59 mole) of phosphorus pentaoxide (effective component: 98.5%) was gradually added thereto. Subsequently, the temperature was raised to 80° C. and reaction was conducted for 12 hours. Furthermore, 72.4 g of ion-exchanged water was added thereto, so as to conduct hydrolysis at 80° C. for 3 hours. Thereafter, this reaction product was subjected to deodorizing treatment using a steam distillatory apparatus (made of glass, heat conducting area: 0.03 m³) through a forcible thin film. The steam distillation was performed by supplying the reaction product and steam continuously at speeds of 100 g/hr. and 75 g/hr., respectively, at a jacket temperature of 150° C. at 2.67 kPa. As a residue, a phosphate containing 0.4% of the organic hydroxy compound and 0.2% of water content was obtained.

Production Example 5

Into a 2000-mL reaction vessel were put 1041.6 g (4.00 moles) of an organic hydroxy compound (average molecular weight=260.4) obtained by adding 2 moles of ethylene oxide to Diadol 11 (average number of carbon atoms: 11, branching fraction: 50%) manufactured by Mitsubishi Chemical Corp., and 93.7 g of 85% by weight orthophosphoric acid (when the acid was represented by $P_2O_5 \cdot nH_2O$, $P_2O_5$: 0.41 mole, $H_2O$: 2.00 moles), and then the resultant was stirred and mixed. While the temperature was kept at 50 to 70° C., 229.6 g (1.59 mole) of phosphorus pentaoxide (effective component: 98.5%) was gradually added thereto. Subsequently, the temperature was raised to 80° C. and reaction was conducted for 12 hours. Furthermore, 72.4 g of ion-exchanged water was added thereto, so as to conduct hydrolysis at 80° C. for 3 hours. Thereafter, this reaction product was subjected to deodorizing treatment using a steam distillatory apparatus (made of glass, heat conducting area: 0.03 m³) through a forcible thin film. The steam distillation was performed by supplying the reaction product and steam continuously at speeds of 100 g/hr. and 75 g/hr., respectively, at a jacket temperature of 150° C. at 2.67 kPa. As a residue, a phosphate containing 0.2% of the organic hydroxy compound and 0.2% of water content was obtained.

Production Example 6

In a 2000-mL reaction vessel, 921.6 g (4.00 moles) of an organic hydroxy compound (average molecular weight=230.4) obtained by adding 1 mole of ethylene oxide to Kalcol 2098 manufactured by Kao Corp., and 93.7 g of 85% by weight orthophosphoric acid (when the acid was represented by $P_2O_5 \cdot nH_2O$, $P_2O_5$: 0.41 mole, $H_2O$: 2.00 moles) were stirred and mixed. While the temperature was kept at 50 to 70° C., 229.6 g (1.59 mole) of phosphorus pentaoxide (effective component: 98.5%) was gradually added thereto. Subsequently, the temperature was raised to 80° C. and reaction was conducted for 12 hours to obtain a phosphate containing 2.4% of ROH and 0.02% of water.

Production Example 7

In a 2000-mL reaction vessel, 1125.6 g (4.00 moles) of an organic hydroxy compound (average molecular weight=281.4) obtained by adding 2 moles of ethylene oxide to Dobanol 23 manufactured by Mitsubishi Chemical Corp., and 93.7 g of 85% by weight orthophosphoric acid (when the acid was represented by $P_2O_5 \cdot nH_2O$, $P_2O_5$: 0.41 mole, $H_2O$: 2.00 moles) were stirred and mixed. While the temperature was kept at 50 to 70° C., 229.6 g (1.59 mole) of phosphorus pentaoxide (effective component: 98.5%) was gradually added thereto. Subsequently, the temperature was raised to 80° C. and reaction was conducted for 12 hours. Furthermore, 72.4 g of ion-exchanged water was added thereto so as to conduct hydrolysis at 80° C. for 3 hours and then obtain a phosphate containing 2.2% of ROH and 4.5% of water.

Production Example 8

In a 2000-mL reaction vessel, 861.6 g (4.00 moles) of an organic hydroxy compound (average molecular weight=215.4) obtained by adding 0.5 mole of ethylene oxide to Neodol 23 manufactured by Shell Chemicals Japan Corp., and 93.7 g of 85% by weight orthophosphoric acid (when the acid was represented by $P_2O_5 \cdot nH_2O$, $P_2O_5$: 0.41 mole, $H_2O$: 2.00 moles) were stirred and mixed. While the temperature was kept at 50 to 70° C., 229.6 g (1.59 moles) of phosphorus pentaoxide (effective component: 98.5%) was gradually added thereto. Subsequently, the temperature was raised to 80° C. and reaction was conducted for 12 hours. Furthermore, 57.0 g of ion-exchanged water was added thereto so as to conduct hydrolysis at 80° C. for 3 hours.Thereafter, the reaction product was subjected to deodorizing treatment using a steam distillatory apparatus (made of glass, heat conducting area: 0.03 m³) through a forcible thin film. The steam distillation was performed by supplying the reaction product and steam continuously at speeds of 100 g/hr. and 75 g/hr., respectively, at a jacket temperature of 150° C. at 2.67 kPa. As residues a phosphate containing 0.5% of ROH and 0.2% of water was obtained.

Production Example 9

In a 2000-mL reaction vessel, 808.8 g (4.00 moles) of an organic hydroxy compound (average molecular weight=202.2) obtained by adding 0.2 mole of ethylene oxide to Neodol 23 manufactured by Shell Chemicals Japan Corp., and 93.7 g of 85% by weight orthophosphoric acid (when the acid was represented by $P_2O_5 \cdot nH_2O$, $P_2O_5$: 0.41 mole, $H_2O$: 2.00 moles) were stirred and mixed. While the temperature was kept at 50 to 70° C., 229.6 g (1.59 moles) of phosphorus pentaoxide (effective component: 98.5%) was gradually added thereto. Subsequently, the temperature was raised to 80° C. and reaction was conducted for 12 hours. Furthermore, 56.6 g of ion-exchanged water was added thereto so as to conduct hydrolysis at 80° C. for 3 hours. Thereafter, the reaction product was subjected to deodorizing treatment using a steam distillatory apparatus (made of glass, heat conducting area: 0.03 m³) through a forcible thin film. The steam distillation was performed by supplying the reaction product and steam continuously at speeds of 100 g/hr. and 75 g/hr., respectively, and at a jacket temperature of 150° C. at 2.67 kPa. As residues a phosphate containing 0.4% of ROH and 0.2% of water was obtained.

Starting organic hydroxy compounds, used to produce phosphates used in examples and comparative example described below, are shown in Table 1.

TABLE 1

| | Starting material alcohol (R1-OH) | average number carbon atoms in R1 | Branching rate of R1 (%) | Average added mole number of PO, n | average added mole number of EO, n |
|---|---|---|---|---|---|
| Example 1 | Kalcol 2098 *1 | 12.0 | 0 | 0 | 1 |
| Example 2 | | | | | |
| Example 3 | Kalcol 0898 *1 | 8.0 | 0 | 10 | 4 |
| Example 4 | | | | | |
| Example 5 | Kalcol 6098 *1 | 16.0 | 0 | 0 | 10 |
| Example 6 | | | | | |
| Example 7 | Dobanol 23 *2 | 12.5 | 25 | 0 | 2 |
| Example 8 | | | | | |
| Example 9 | Diadol 11 *2 | 11.0 | 50 | 0 | 2 |
| Example 10 | | | | | |
| Example 11 | Neodol 23 *3 | 12.5 | 20 | 0 | 0.5 |
| Example 12 | | | | | |
| Example 13 | Neodol 23 *3 | 12.5 | 20 | 0 | 0.2 |
| Example 14 | | | | | |
| Comparative example 1 | Kalcol 2098 *1 | 12.0 | 0 | 0 | 1 |
| Comparative example 2 | | | | | |
| Comparative example 3 | Kalcol 2098 *1 | 12.0 | 0 | 0 | 1 |
| Comparative example 4 | | | | | |
| Comparative example 5 | Dobanol 23 *2 | 12.5 | 25 | 0 | 2 |
| Comparative example 6 | | | | | |

*1 manufactured by Kao Corp.,
*2 manufactured by Mitsubishi Chemical Corp.,
*3 manufactured by Shell Chemicals Japan Corp.

Examples 1 to 14

A phosphate was obtained by performing procedures of Production Example 1 to 5, 8 and 9 and mixing the product with ion-exchanged water and components b and c at the ratios shown in Table 2. The resultant phosphates were put into a hot wind drying machine the temperature of which was adjusted to 50° C., and then the amount of dioxane in each of the mixtures was measured after one to 3 months. The odor thereof was evaluated.

Comparative Examples 1 to 6

A phosphate was obtained by performing procedures of Production Example 1, 6 and 7 and mixing the product with components b and c at the ratios shown in Table 3. The resultant phosphates were put into a hot wind drying machine the temperature of which was adjusted to 50° C., and then the amount of dioxane in each of the mixtures was measured after one to 3 months. The odor thereof was evaluated.

The evaluation was made with the following criterion. Dioxane; a gas chromatograph ("HP-6890", manufactured by Agilent Co.) was used to measure gas generated by means of a head space sampler by a standard addition method. Head space sampler; "HP-7694", manufactured by Agilent Co. Gas chromatograph; "HP-6890", manufactured by Agilent Co. Odor; it was judged by 10 panels whether or not a bad odor was generated in accordance with the following criterion:

◎: No bad odor is recognized.

◯: A bad odor is slightly recognized.

Δ: A slightly strong bad odor is recognized.

×: A strong bad odor is recognized.

××: A very strong bad odor is recognized.

TABLE 2

| | | | Example of Present invention | | | | | | | | | | | | | |
|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 |
| Charged quantity | Phosphate | Production example 1 | 94.9 | 90.9 | | | | | | | | | | | | |
| | | Production example 2 | | | 93.9 | 87.0 | | | | | | | | | | |

TABLE 2-continued

|  |  |  | Example of Present invention | | | | | | | | | | | | | |
|---|---|---|---|---|---|---|---|---|---|---|---|---|---|---|---|---|
|  |  |  | 1 | 2 | 3 | 4 | 5 | 6 | 7 | 8 | 9 | 10 | 11 | 12 | 13 | 14 |
| (weight-%) |  | Production example 3 |  |  |  |  | 94.4 | 85.0 |  |  |  |  |  |  |  |  |
|  |  | Production example 4 |  |  |  |  |  |  | 88.9 | 91.9 |  |  |  |  |  |  |
|  |  | Production example 5 |  |  |  |  |  |  |  |  | 99.0 | 69.9 |  |  |  |  |
|  |  | Production example 8 |  |  |  |  |  |  |  |  |  |  | 94.9 | 90.9 |  |  |
|  |  | Production example 9 |  |  |  |  |  |  |  |  |  |  |  |  | 93.4 | 88.4 |
|  | Component b | Ethanol | 3.0 |  |  |  | 5.0 | 10.0 |  |  |  | 20.0 | 3.0 |  | 5.0 |  |
|  |  | Propylene glycol | 1.0 |  | 5.0 |  |  |  |  | 5.0 |  |  | 1.0 |  |  |  |
|  |  | Dipropylene glycol |  | 8.0 |  | 10.0 |  |  | 10.0 |  |  |  |  | 8.0 |  | 10.0 |
|  | Component c | BHT | 0.1 | 0.1 | 0.1 |  | 0.1 |  | 0.1 | 0.1 |  | 0.1 | 0.1 | 0.1 | 0.1 | 0.1 |
|  |  | Ion-exchanged water | 1.0 | 1.0 | 1.0 | 3.0 | 0.5 | 5.0 | 1.0 | 3.0 | 1.0 | 10.0 | 1.0 | 1.0 | 1.5 | 1.5 |
| Stabilization test (50° C.) | Initial stage | Dioxane (mg/kg) | <1 | <1 | <1 | <1 | <1 | <1 | <1 | <1 | <1 | <1 | <1 | <1 | <1 | <1 |
|  |  | Odor | ◉ | ◉ | ◉ | ◉ | ◉ | ◉ | ◉ | ◉ | ◉ | ◉ | ◉ | ◉ | ◉ | ◉ |
|  | After 1 month | Dioxane (mg/kg) | 4 | 4 | 5 | 4 | 6 | 5 | 4 | 4 | 4 | 3 | 3 | 3 | 3 | 3 |
|  |  | Odor | ◉ | ◉ | ◉ | ○ | ◉ | ○ | ◉ | ◉ | ○ | ◉ | ◉ | ◉ | ◉ | ◉ |
|  | After 2 months | Dioxane (mg/kg) | 12 | 10 | 15 | 10 | 20 | 15 | 10 | 10 | 10 | 8 | 10 | 9 | 8 | 6 |
|  |  | Odor | ○ | ○ | ○ | ○ | ○ | ○ | ○ | ○ | ○ | ○ | ○ | ○ | ○ | ○ |
|  | After 3 months | Dioxane (mg/kg) | 26 | 25 | 28 | 24 | 30 | 27 | 25 | 26 | 27 | 25 | 25 | 24 | 20 | 18 |
|  |  | Odor | ○ | ○ | ○ | △ | ○ | △ | ○ | ○ | △ | ○ | ○ | ○ | ○ | ○ |

TABLE 3

|  |  |  | Comparative example | | | | | |
|---|---|---|---|---|---|---|---|---|
|  |  |  | 1 | 2 | 3 | 4 | 5 | 6 |
| Charged quantity (weight-%) | Phosphate | Production example 1 | 91.9 | 100 |  |  |  |  |
|  |  | Production example 6 |  |  | 93.9 | 100 |  |  |
|  |  | Production example 7 |  |  |  |  | 89.9 | 100 |
|  | component b | Ethanol | 3.0 |  | 5.0 |  |  |  |
|  |  | Propylene glycol | 5.0 |  |  |  |  |  |
|  |  | Dipropylene glycol |  |  | 1.0 |  | 10.0 |  |
|  | component c | BHT | 0.1 |  | 0.1 |  | 0.1 |  |
|  |  | Ion-exchanged water |  |  |  |  |  |  |
| Stabilization test (50° C.) | Initial stage | Dioxane (mg/kg) | <1 | <1 | 38 | 40 | 45 | 50 |
|  |  | Odor | ◉ | ◉ | × | × | × | × |
|  | After 1 month | Dioxane (mg/kg) | 30 | 40 | 100 | 105 | 50 | 58 |
|  |  | Odor | ◉ | ◉ | ◉ | ○ | ◉ | ○ |
|  | After 2 months | Dioxane (mg/kg) | 210 | 270 | 280 | 340 | 60 | 69 |
|  |  | Odor | △ | × | × × | × × | × × | × × |
|  | After 3 months | Dioxane (mg/kg) | 480 | 570 | 550 | 650 | 75 | 85 |
|  |  | Odor | × | × × | × × | × × | × × | × × |

The invention claimed is:

1. A process for producing a phosphate, comprising the following steps 1, 2 and 3:

step 1: the step of reacting an organic hydroxy compound represented by the following general formula (I) with at least one phosphorylating agent selected from the group consisting of orthophosphoric acid, phosphorus pentaoxide, and polyphosphoric acid:

$$R^1—O—(AO)_n—H \quad (I)$$

wherein $R^1$ represents a straight or branched alkyl group or alkenyl group having 6 to 36 carbon atoms, AO represents an oxyalkylene group having 2 to 4 carbon atoms and n is a number of 0.1 to 100 on the average;

step 2: the step of purifying the reaction product obtained in the step 1 until the content of the organic hydroxy compound that has not yet reacted becomes 2% or less by weight; and step 3: the step of adding water to the purified product obtained in the step 2 at such a ratio that the content of water in the final product is from 0.5 to 30% by weight.

2. The process according to claim 1, which, in the step 3, further comprises adding at least one selected from the group consisting of alcohols having 1 to 4 carbon atoms and glycols represented by the following general formula (II):

$$HO—(R^2O)_m—H \quad (II)$$

wherein $R^2$ represents an alkylene group having 2 to 4 carbon atoms, and m is a number of 1 to 3.

3. The process according to claim 1 or 2, which, in the step 3, further comprises adding an antioxidant.

4. The process according to claim 1, wherein the phosphorylating agent is orthophosphoric acid.

5. The process according to claim 1, wherein the phosphorylating agent is phosphorus pentaoxide.

6. The process according to claim 1, wherein the phosphorylating agent is a polyphosphoric acid.

7. The process according to claim 1, wherein the final product is a phosphate adduct with the organic hydroxy compound.

8. The process according to claim 1, wherein in step 2 the content of the organic hydroxy compound that has not yet reacted is 1.5% or less by weight.

9. The process according to claim 1, wherein the purifying of step 2 is at least one of extraction or crystallization.

10. The process according to claim 1, wherein the purification of step 2 is distillation.

11. The process according to claim 1, wherein the antioxidant is at least one selected from the group consisting of di-t-butylhydroxy toluene, di-t-butylhydroxy anisole, dl-α-tocopherol, and isopropyl gallate.

12. The process according to claim 1, further comprising: neutralizing the phosphate.

13. The process according to claim 1, wherein the organic hydroxy compound is obtained by reacting ethylene oxide and lauryl alcohol.

14. The process according to claim 1, wherein in step 1 the organic hydroxy compound is first reacted with orthophosphoric acid and then reacted with phosphorus pentoxide.

15. The process according to claim 1, wherein the organic hydroxy compound is obtained by reacting propylene oxide with octyl alcohol and ethylene oxide.

16. A phosphate obtained by the process as claimed in claim 1.

17. The phosphate as claimed in claim 16, comprising less than 1 mg/kg of dioxane.

18. The process according to claim 1, wherein n is a number of 0.1 to 50 on the average.

19. The process according to claim 1, wherein n is a number of 0.1 to 20 on the average.

* * * * *